United States Patent
Fucile

(10) Patent No.: US 7,034,327 B2
(45) Date of Patent: Apr. 25, 2006

(54) EXPENDABLE OCEANOGRAPHIC DIGITAL COMMUNICATIONS SYSTEM

(75) Inventor: Paul D. Fucile, East Falmouth, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 0 days.

(21) Appl. No.: 10/444,590

(22) Filed: May 23, 2003

(65) Prior Publication Data

US 2003/0198297 A1    Oct. 23, 2003

Related U.S. Application Data

(63) Continuation of application No. 09/021,242, filed on Feb. 10, 1998, now Pat. No. 6,570,176.

(60) Provisional application No. 60/038,155, filed on Feb. 10, 1997.

(51) Int. Cl.
  *G01N 15/06* (2006.01)
(52) U.S. Cl. ........................ 250/573; 398/104
(58) Field of Classification Search ................ 250/573, 250/239; 398/104, 105
  See application file for complete search history.

(56) References Cited

U.S. PATENT DOCUMENTS

| | | | | |
|---|---|---|---|---|
| 4,280,221 A | * | 7/1981 | Chun et al. | 375/288 |
| 4,480,323 A | * | 10/1984 | Page | 367/131 |
| 4,557,608 A | * | 12/1985 | Carver | 374/170 |
| 4,804,849 A | * | 2/1989 | Booth et al. | 250/459.1 |
| 4,978,854 A | * | 12/1990 | Lapota et al. | 250/361 C |
| 5,170,379 A | * | 12/1992 | Ruzie et al. | 367/106 |
| 5,767,682 A | | 6/1998 | Sekimoto et al. | |

* cited by examiner

*Primary Examiner*—Thanh X. Luu

(74) *Attorney, Agent, or Firm*—Hamilton, Brook, Smith & Reynolds, P.C.

(57) ABSTRACT

A bathyphotometer system is described for detecting photoluminescent signals excited by a grid disposed in a marine vehicle. The system uses photodiodes to convert the optical signals into electrical signals which are sampled, integrated and coupled to output terminals for transmission to a surface host vehicle. In one embodiment the signals are digitized and encoded as FSK tones for transmission to the surface host vehicle.

11 Claims, 9 Drawing Sheets

EXPENDABLE OCEANOGRAPHIC DIGITAL COMMUNICATIONS SYSTEM

RELATED APPLICATIONS

This application is a continuation of U.S. application Ser. No. 09/021,242, filed Feb. 10, 1998, now U.S. Pat. No. 6,570,176, which claims the benefit of U.S. Provisional Application No. 60/038,155 filed Feb. 10, 1997, the teachings of which are incorporated herein by reference in their entirety.

FIELD OF THE INVENTION

This invention relates to the field of detecting and measuring bioluminescence.

BACKGROUND OF INVENTION

Specifically the present invention relates to in situ measurements of bioluminescence intensity in the ocean and other bodies of water. Bioluminescence is one measure of the number and type of organisms in water, which is helpful in understanding population dynamics and certain sound transmission characteristics of water.

Bioluminescence in aquatic environments comes from a wide variety of sources. Tett and Kelly (Oceanogr. Mar. Biol. Ann. Rev, 1973, p 89–173) gives a detailed review of the physics of the measurements, and a phyletic review. Many different species, belonging to most of the phyla exhibit bioluminescence, including Bacteria, Dinoflagellates, Radiolaria, Hydrozoa, Siphonophora, Scyphozoa, Anthozoa, Ctenophora, Polychaeta, Lamellibrachiata, Cephalopoda, Crustacea, Urochordata and Actinopterygii. Studies indicate that these organisms use bioluminescence for a great variety of vital functions. It is an important mechanism for understanding physiological processes. Work has shown that certain species can be identified on the basis of their bioluminescence. Clearly it is one of the commonest radiative processes of organisms as well as one of the most complex. As such, a considerable body of research has accumulated; in fact there is a Journal of Bioluminescence and Chemiluminescence.

Beginning in the 1940's, instrumentation for quantitative measurements of bioluminescence was developed in several countries. Yentsch and Yentsch (Oceanogr. Maar. Biol. Ann. Rev, 1984, p 55–98), and Gitelson and Levin (Jour Bioluminescence and Chemiluminescence, 1989, p 555–562) describe some of the technology. A more recent paper by Case et al, (Naval Research Reviews, Two 1993, p 31–41) gives a good overview and bibliography. Also, there are several U.S. patents describing techniques and instrumentation for observing bioluminescence. See for example:

U.S. Pat. No. 4,563,331 to Losee and Lapota, "System for measuring bioluminescence flash kinetics"
U.S. Pat. No. 4,689,305 to Stiffey, Blank and Loeb, "Solid-state photometer circuit"
U.S. Pat. No. 4,978,854 to Lapota, Mastny, Copeland, "Bioluminescent detector"
U.S. Pat. No. 5,264,906 to Fever, Case, Widder, Bernstein, Lowenstine, "Biolumescence bathyphotometer"
U.S. Pat. No. 5,554,035 to Gooch, "Bioluminescent algae in light bulb shaped viewing device"
U.S. Pat. No. 5,565,360 to Lapota, Mastny, Copeland, Rosenberger, "Biolumescent bioassay system"

The foregoing instrumentation literature and patents describe tailored systems for fairly specific applications, such as laboratory apparatus to study isolated organisms, or determination of organism response to certain physical or chemical stimulus.

SUMMARY OF THE INVENTION

The specificity of the foregoing research objectives overlooks the more flexible observation strategies available in accordance with the present invention which utilizes a suite of small, inexpensive, stable, robust building blocks to make, in concert with other sensors, practical synoptic observations of bioluminescence at ocean fronts, where differing water masses meet.

Accordingly, the present invention provides an economical underway bioluminescence detector that can be used for vertical profiles, horizontal profiles at a fixed depth, or in a vertically undulating mode. The detector is compact and can be attached to a towed or autonomous underwater vehicle (AUV). The vehicle's motion causes water to flush through a grid in the detector housing to generate the requisite turbulence within the instrument for stimulation of luminescent organisms, which provides a measurement of bioluminescence. The detector can also be used for moored (stationary) applications.

In a preferred embodiment of the invention a submersible bioluminescence detector system is comprised of a housing having an inlet port and an outlet port and a grid disposed at the inlet port in the path of water entering the inlet port to exite organisms in the water to exhibit bioluminescence. The bioluminescence is detected by a photodetector disposed in an hermetically sealed optically clear envelope facing the grid. The biodetector generates a first bioluminescence electrical signal. An analog or digital circuit samples, integrates and amplifies the electrical signal and transmits the signal to a host computer for further processing and display.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
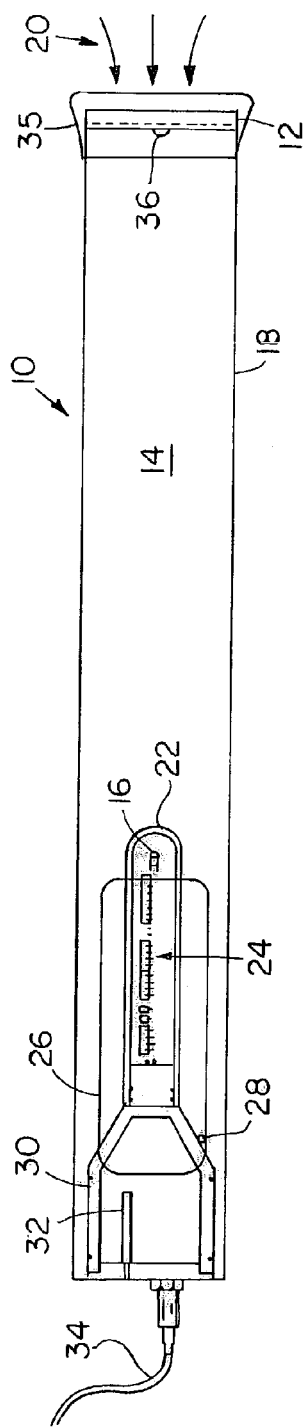
FIG. 1 is a schematicized side sectional diagram of a first embodiment of a bioluminescence detector of the invention showing major components.
Figure 7:
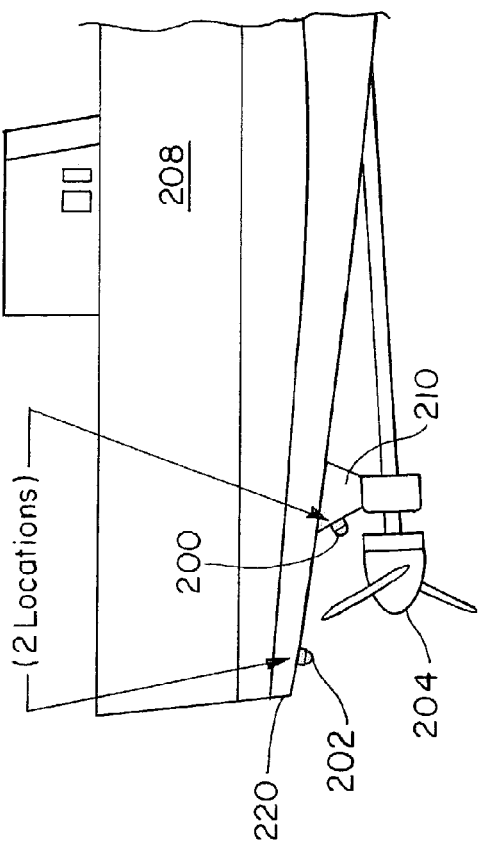
FIG. 7 is a schematic view of an unshrouded propeller detector version of the invention.

Referring now to FIGS. 1 and 2, a first embodiment of the invention will now be described in connection therewith. In its simpler form as shown in FIG. 7, the device consists of a bioluminescence detector 10 having an excitation device such as a grid 12, a viewing chamber or observing tube 14, and a detector 16. A flow of water 20 passes through the grid and detector as the device is towed along the water. The detector 16 is housed in a transparent inner envelope or housing 22 made of, for example, glass. Associated electronics 24 may also be mounted in housing 22. The housing or envelope 22 is enclosed in a chamber 26 which is provided with exhaust flutes (not shown) to enable the incoming water 20 to escape. An optional bead thermistor 28 is mounted inside chamber 26 to measure the water temperature. Support bracket 30 is attached to an end of the outer housing or viewing tube 18 opposite excitation grid 12. A pressure transducer 32, a power/data cable 34 coupled to an external host on a towing vehicle and the inner housing 22 are mounted on bracket 30. An optional aft viewing photo detector 36 is mounted adjacent grid 12 facing the first photodiode 16.

The apparatus of FIG. 1 provides a simple interface for commonly used data collection systems, the detector system can be adapted to a number of existing underwater vehicles, instrumented platforms, or can be mounted to the hull of a ship. As will be shown in connection with FIG. 3, the low power requirements for the detector 16 eliminate the need for a dedicated power source, allowing operating power to be drawn from the data acquisition system via the data cable 34.

The observing tube 14 is typically fabricated of a plastic such as polyvinyl chloride, and is preferably about 50 cm in overall length with openings at each end typically 5 to 10 cm in diameter. The volume viewed by the sensor 16 is typically 12 to 20 cm deep giving a particle residence time of 30 to 40 ms when the device 10 is towed at 8 kts. The straight flow-through of water 20 obviates the need for pumps or impellers which require power and control. Measurement of flow through the sensor, or a flow calibration based on the motion of the vehicle on which the sensor is mounted may be required however. The overall tube length to diameter ratio is important in determining the actual water flow through the sensor at a given vehicle velocity. A ratio of less than 5 has been found preferable to that used in the past where the flushing rate is insufficient.

Figure 8C:
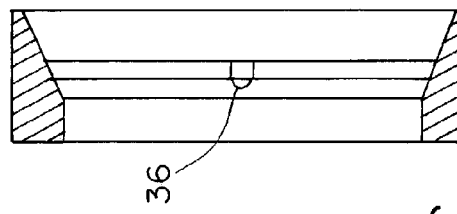
FIG. 8C is a side view of an excitation grid.
Figure 8B:
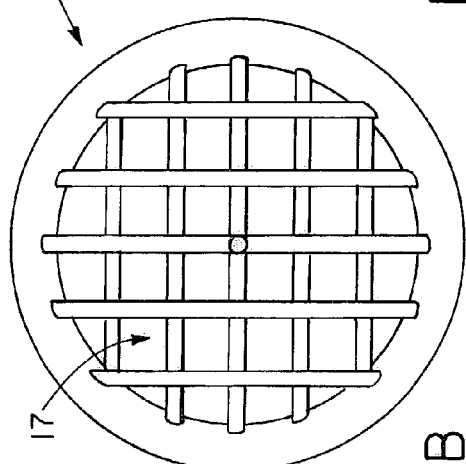
FIG. 8B is a back view of an excitation grid.
Figure 8A:
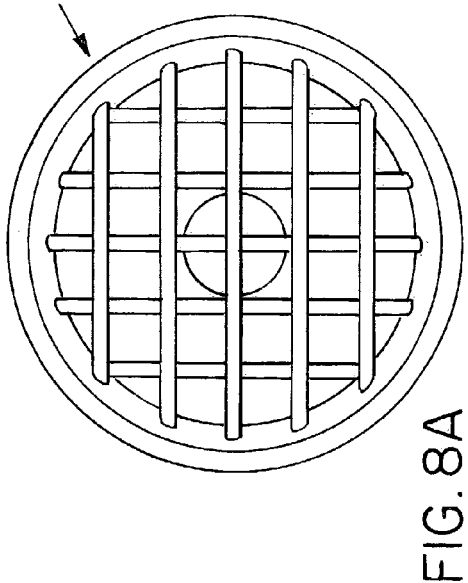
FIG. 8A is a front view of an excitation grid.

The excitation grid 12, (see FIG. 8) typically has a grid spacing 17 of 1 cm and a diameter of about 5 cm. The grid is held in place with a removable ring 15 or is laced with light gauge stainless steel wire (not shown). Other grid spacings or geometries can be easily substituted. Grid materials are typically plastics, stainless steel or other non-reactive metals. On systems requiring flash kinetics or relatively long residence times, an aftward facing photo-diode 36 is implemented. To reduce drag, it is embedded in the plastic of a center grid structure as shown. The detector will observe any organism up to the size of the excitation grid 12.

The need to minimize ambient light background is addressed by blackening the exterior walls 18 of the viewing chamber 14 and grid; or mounting the device 10 in a shaded location on the host vehicle (not shown).

By keeping the drag minimal with a small physical size, the detector system 10 can be adapted to a number of existing towed or self-propelled underwater vehicles (AUVs). Mounting to the host can be achieved by a simple clamp assembly, or the use of fasteners extending through the chamber wall 18. Depending on where the detector 10 is mounted on the host vehicle, a calibration should be made for the flow rate through the detector versus the speed of the host vehicle. The robust construction of the system 10 allows it to be used at the maximum speed or depth of any known vehicle in the ocean.

The end of the viewing tube 14 may be provided with a zinc ring weight 35 at the intake end to provide a drop rate of a nominal 4 meters/sec. In an expendable version the tapered trailing end may contain a supply of wire (not shown) that spools off as the probe drops away. A small onboard battery (not shown) may provide power to operate the device for 45 minutes, although a 350 meter drop takes only 90 seconds. Data frames are transmitted at 10 frames/sec.

Figure 2A:
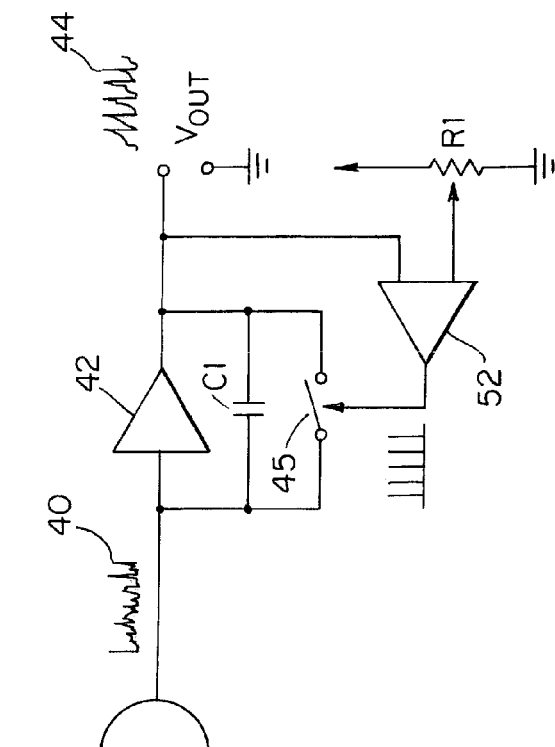
FIG. 2A is a circuit block diagram of the detector of FIG. 1.
Figure 2B:
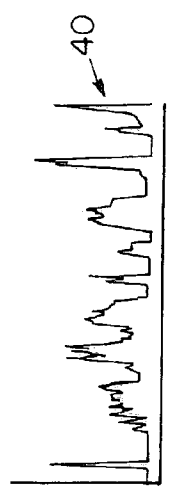
FIG. 2B is a plot of the output signal 40 of the photo detector 16 of FIG. 2A.
Figure 2C:
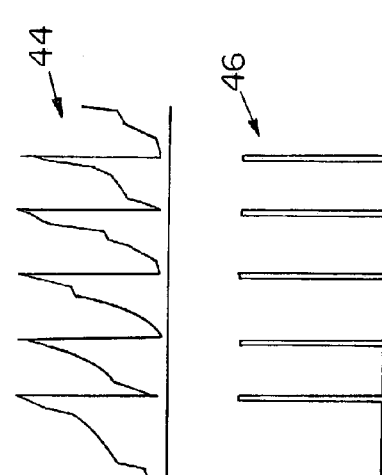
FIG. 2C is a plot of the voltage output signal 44 of FIG. 2A.
Figure 2D:
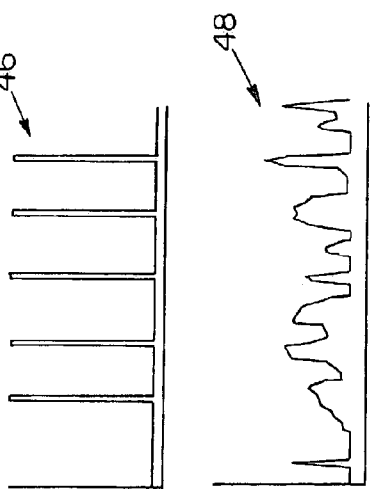
FIG. 2D is a plot of the integrator reset signal 46 of FIG. 2A.

Previous bathyphotometer designs rely on a Photo Multiplier Tube (PMT). The high sensitivity of a PMT is desirable, but practical concerns are the high voltage supply associated with PMT's, the inability to operate in daylight without damage, and the physical size of such an assembly. The alternative technology used herein is the photodiode with a sensitivity below that of the PMT. An optimized photodiode will, however, measure bioluminescent activity. When constructing a photodiode based detector as shown in FIG. 2A, the primary limits are noise current and the device capacitance between the diode and the amplifier. By using an integrating transimpedance amplifier, as described herein, sensor noise with sensor signal 40 (FIG. 2B) is averaged and subsequently reduced. Rather than using high feedback resistors (>10 M Ohms) as in conventional amplifiers, a combination of a small integrating capacitor C1 and the modest integrating time of integrator 42 provides equivalent or better gains than obtainable with feedback resistor topologies.

Figure 3:
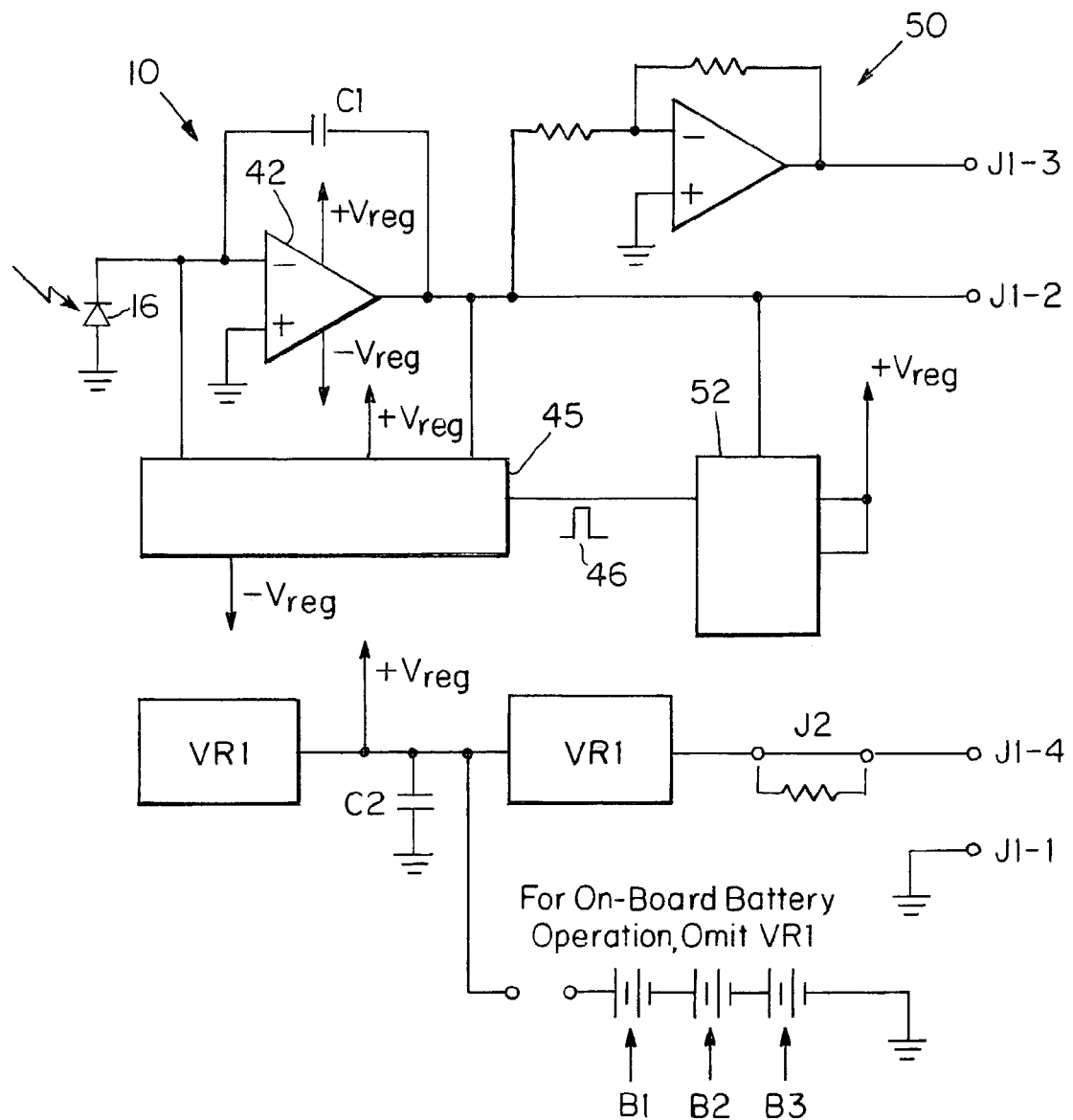
FIG. 3 is a detailed circuit diagram of the detector of FIG. 1.

A detail diagram of the sensor circuit of FIG. 2A is shown in FIG. 3.

Figure 2E:
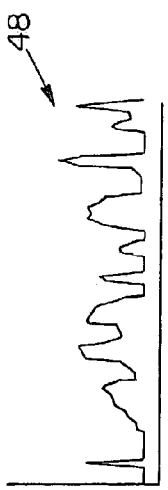
FIG. 2E is a plot of the $V_{out}$ signal 48 after it is processed at a 24 Hz dV/dt data rate.

This circuit uses a 7.75 mm$^2$ surface area photodiode that injects current into an integrator circuit 42. When the output signal 44 (FIG. 2C) reaches a specified threshold, say 4.75 volts, the integrator is reset by analog switch 45. The system then proceeds to integrate from zero volts again. This handles the broad band of biological light signals found in the ocean, ranging from discrete flashes to continuums. The data are analyzed by measuring the voltage and taking the differential from the previous measurement as output signal 48 (FIG. 2E). Any output condition that results in a negative value triggers an integrator reset signal 46 (FIG. 2D) from one-shot multi-vibrator 52. The magnitude of the signal for each period is linearly related to the light detected. Sensitivity and dynamic range is a function of sampling frequency and the integrating capacitor C1. This detector system permits use of a relatively slow acquisition speed (<25 Hz), for example, and a use of auxiliary conductivity, temperature and depth recording (CTD) measurement devices, to quantify activity between sensor sampling points.

Where there is connectivity to the observing ship (not shown), a real time computer program can be used to display the data.

Gain is set by the value of the integrating capacitor C1. An inverting amplifier stage 50, coupled to the output of integrator 42 is also provided for driving balanced output bifilar wire or twisted pairs in excess of 500 meters (not shown), coupled across jacks J1-2 and J1-3. An electronic analog switch in parallel with the integrating capacitor (C1) allows the integrator 42 to be reset. To perform resets, the aforementioned monostable multivibrator 52 is used to detect the reset threshold voltage (nominally 4.75 volts) from integrator 72 and to provide a uniform logic level reset pulse for the integrator. This reset is required to make the circuit stable, otherwise a race condition could exist.

Power for the electronics may be derived, from an external DC source (not shown) via J1-4 and is regulated to 9 volts by an onboard voltage regulator VR1. Alternatively, by reconfiguring the circuit as shown, the device can be made to operate from three coin type batteries B1, B2, B3 in Series or a single 9V equivalent.

This self-contained active detector 10 with driver circuit 50 has the ability to drive signals over long lengths of wire, thus the sensor could be deployed in an expendable manner from aircraft or other high speed vessels. This active solution is an improvement over prior art expendable devices since it overcomes the Johnson noise attributed to wire resistance and bandwidth limitations due to wire capacitance. For the lowest level of observable bioluminescence, the passive design of the prior art can not overcome its inherent noise floor. For the present active system, even the brightest observable measurements, or even with the sensor on deck during daylight for that matter, the highest integrating ramp up frequency does not exceed 500 Hz, which is well within the bandwidth for expendable bifilar wire technologies. The analog amplifier of FIG. 3 has excellent stability in high vibration environments such as those experienced by underwater vehicles; far better than PMT's.

Figure 4:
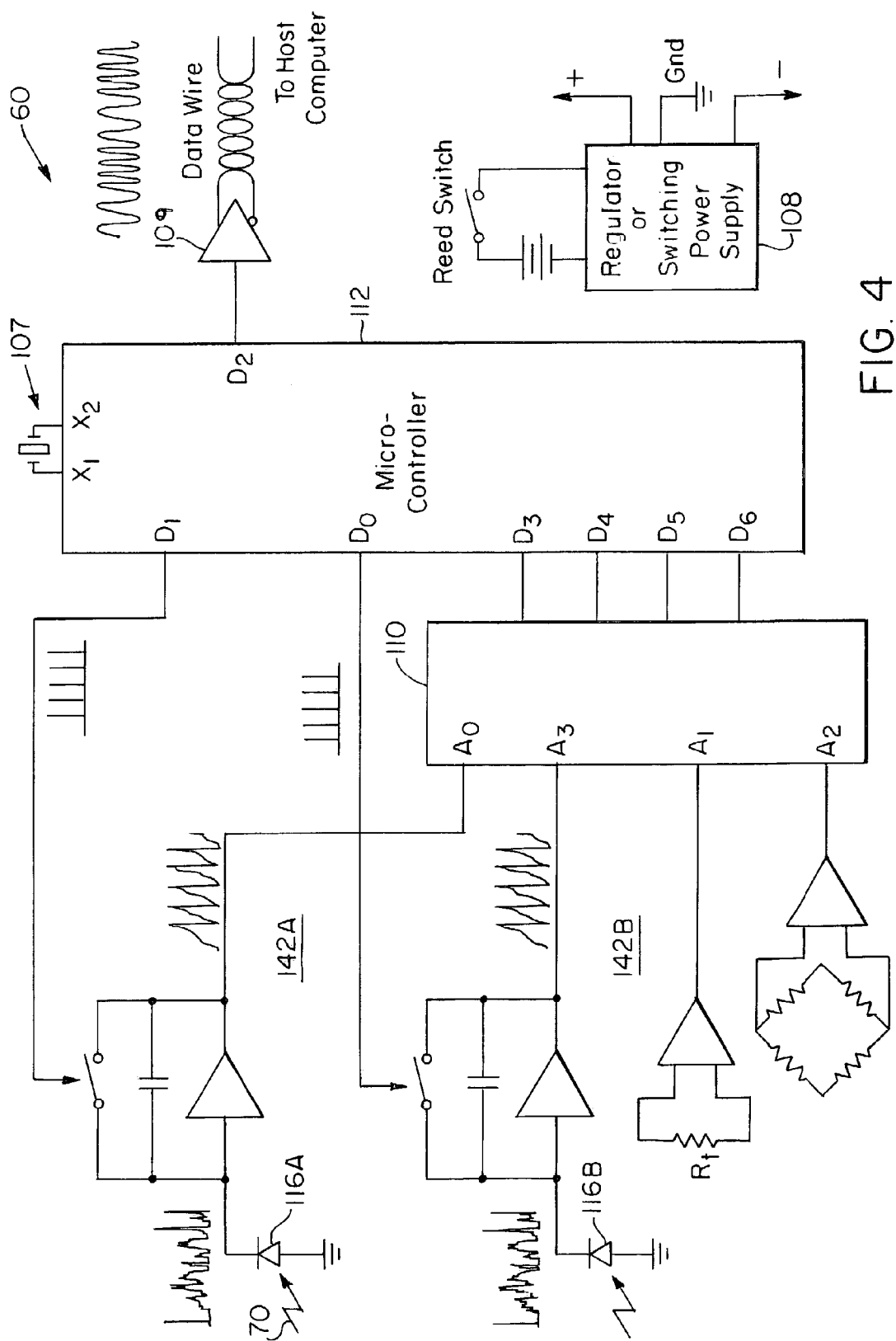
FIG. 4 is a circuit block diagram of a second embodiment of a bioluminescence detector of the invention.

For more demanding applications, a second preferred embodiment will now be described in the form of the digital system 60 of FIGS. 4–6. The fundamental improvements provided by the digital system are the ability to perform two or more zone light measurements, direct pressure (depth), and temperature measurement, digital programmability, economy, and digital data transmission. Referring now to the block diagram of FIG. 4 and the circuit of FIGS. 5A–B there is shown a first forward looking photodiode 116A which detects bioluminescence 70 and injects current into an integrator 142A. At a fixed rate (say 160 Hz) the output A0 of the integrator 142A is digitized in A-D converter 110. If the value is below a low end threshold (6.25% of full scale), the integrator 142A is not reset. If the output value, however, is above this low end value, the integrator 142A is reset by a reset signal from microcontroller 112 on line RBO and the output value is summed into a register (not shown) in microcontroller 112. The dynamic range, now becomes a function of how often the integrator can be read and potentially reset. Since this device supports multi-channel analog to digital conversions, temperature and pressure sensors RT and PZ respectively measure pressure and temperature directly and these values are coupled to A-D converter 110 on lines A1, A2, respectively.

The detector of FIG. 4 can be used to measure bioluminescence from two zones, i.e., forward and aft as will be described in detail below in connection with the schematic of FIGS. 5A–B. For a two zone measurement two problems must be solved. First, the fundamental optical source to detector problem of $1/r^2$ light extinction is addressed by detecting synoptically the light field in the chamber. In theory, a point light source that is 10 cm from the detector is measured at only 1% of its actual value. In practice however, a point source in a chamber with reflecting walls is measured at 10% of its actual value. Since the chamber length is dictated by the requirement for certain residence times, the preferred overall chamber length is typically 50 cm and the sensor/detector may be located about 20 cm from the grid. As noted previously, a second sensor 36 is provided for viewing aft of the flow to improve this measurement. By measuring both fields of light, the light source can be determined as being bright and far away, bright and close, or not so bright and close, relative to each of the detectors.

The second problem relates to the study of bioluminescence known as flash kinetics. Certain species of bioluminescent organisms, may flash bright when initially striking the grid 12, and then decay fast enough to not contribute significant light when close to the detector. Others may ramp up to full brightness just in time to be measured in close proximity to the sensor. By comparing both synoptic measurements, fundamental kinetics can be determined.

Figure 5A:
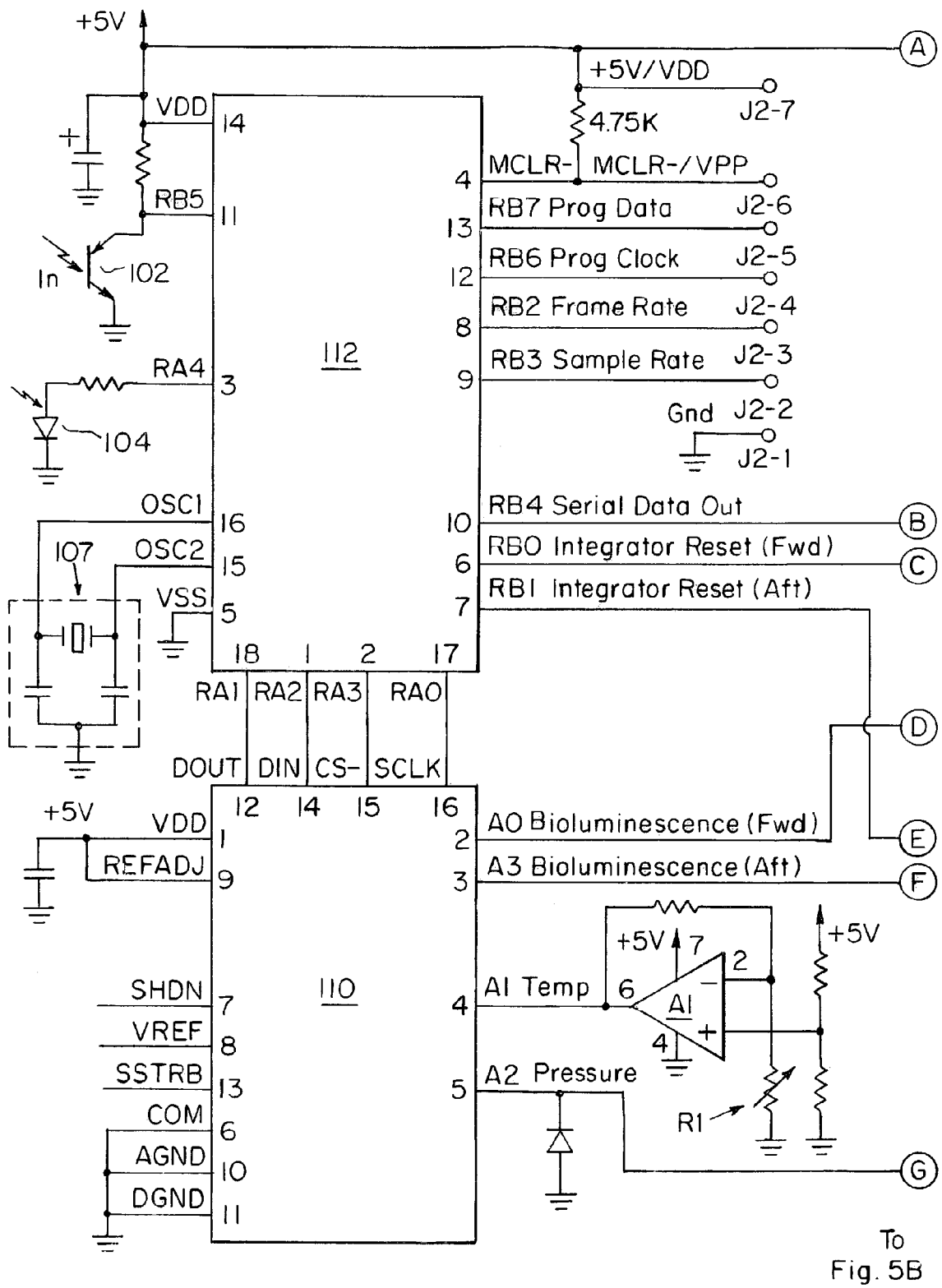
FIG. 5A is a detail circuit diagram of the detector of FIG. 4.
Figure 5B:
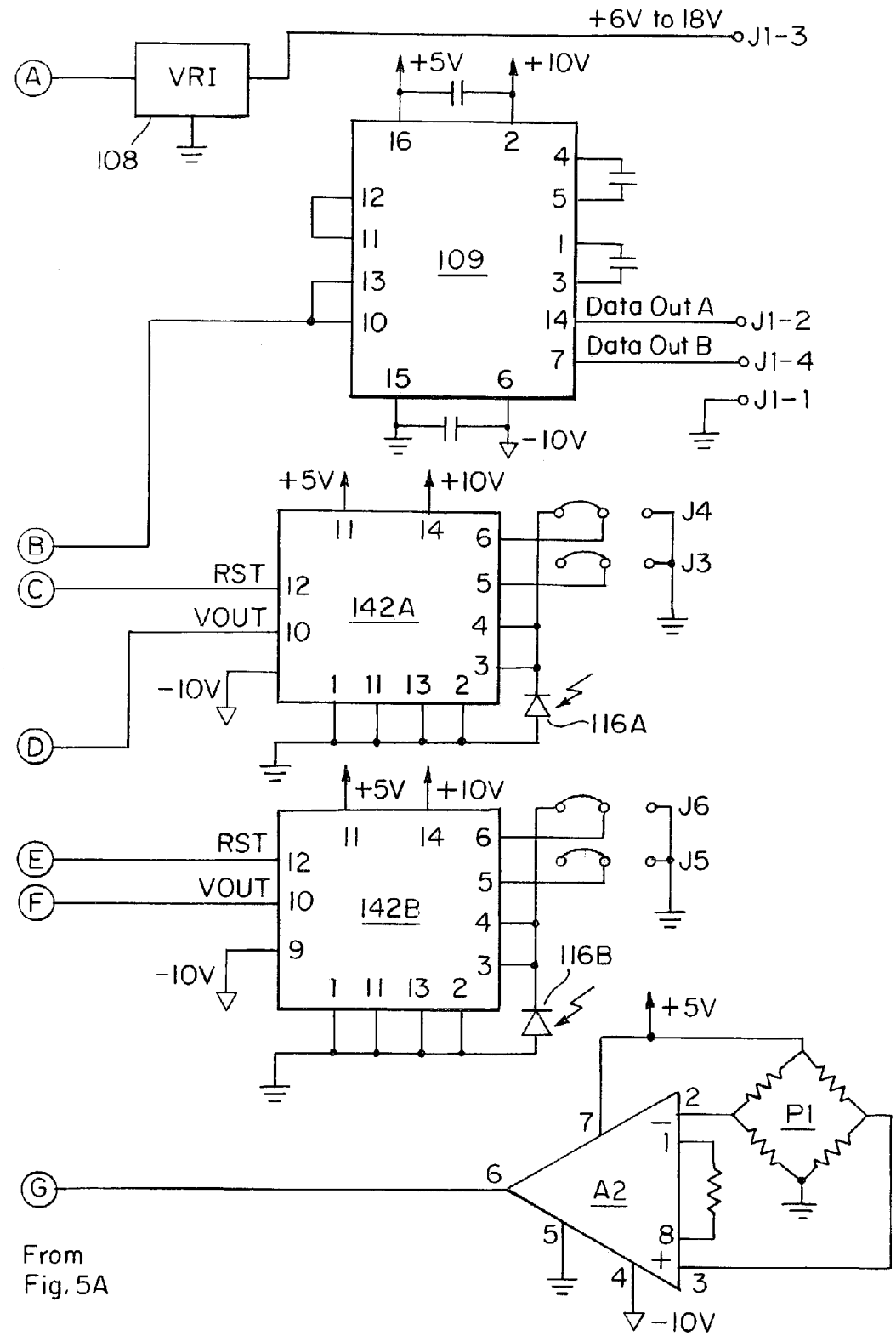
FIG. 5B is a detail circuit diagram of the detector of FIG. 4.

A schematic diagram showing further details of the two zone circuit is shown in FIGS. 5A–B. The key components are the aforementioned PIC microcontroller 112, two self contained integrating amplifiers 142A, 142B and photodiodes 116A, 116B, respectively for the forward and aft sensors; a thermistor R1 and temperature amplifier A1, a pressure transducer P1 and an instrumentation amplifier A2, a four channel 12 bit analog to digital converter 110, and a line level driver 109. A voltage regulator 108 and/or a battery is provided depending upon whether a battery on board system is required or not. The system may be powered externally via jack J1-3. The PIC operates at 4 MHz as controlled by clock oscillator 107 which gives it a fast enough instruction time to encode the data from the sensors as Frequency Shift Keying (FSK) tones or other software UART outputs to balanced output line driver 109. Power may be supplied from an external host in the range of 6 to 18 V at a nominal current of 20 mA at input jack J1-3 to voltage regulator 108. For single zone measurements, the Aft viewing integrator 142B and photodiode 116B may be removed. Gain is governed by the value of the integrating capacitor (not shown) and can be set at a span of 10 to 1 by using jumpers J3 and J4 coupled to terminals 5 and 6 of integrating amplifier 142A for the Forward viewing sensor 116A, and jacks J5 and J6 for the Aft viewing sensor 116B. Temperature compensation is provided as a correction derived from the onboard temperature measurement from the A1 input to terminal 4 of A-D converter 110. For EIA-232 outputs at J1-2, the signal is taken directly from the line driver 109 Output line A at terminal 14 with respect to ground. For FSK or differential baseband signals similar to EIA-485 driving an expendable bifilar wire, or a long submarine cable, the signals are taken from the line driver 109 as true and inverted signals. Connector jacks J2-1 through 4 on microcontroller 112 are used for calibration of Frame, Sample Rate, and power supply status. Two jacks J2-4 and 5 are also provided for "in circuit" programming as supported by the PIC microcontroller 112. Optical data input and output signaling is provided by a photo transistor 102 and light emitting diode 104 pair. These may be used for communications through the glass envelope 22 of FIG. 1.

The optical data feature is intended for use in a "smart" expendable launcher that will communicate directly with the device 10 checking clock speed and calibration parameters. The expendable launcher would also have the ability to pass commands to operate at a different sampling rate prior to launch.

As previously noted; power for the device may also be provided by an onboard battery, and there are a number of options for self powering of the circuit. One is to use a miniature battery in the range of 9 to 12 volts with the existing voltage regulator. The second is to use 2 coin type batteries to generate 6 volts. All the parts used in the circuit operate in the range of 4 to 6 volts and will stay in specification. Both temperature and pressure are made as ratiometric measurements and therefore offer excellent power supply variation error rejection.

A host real time data display (not shown) can provide graphical representations of probe depth and fall rates, temperature, and bioluminescence from the data collected by the device 10.

Since the data stream are audio bandwidth frequencies, simple transmitters can be used making air dropped expendable bioluminescence detectors economically feasible. The pressure sensor is of an economical surface mount type.

Figure 6:
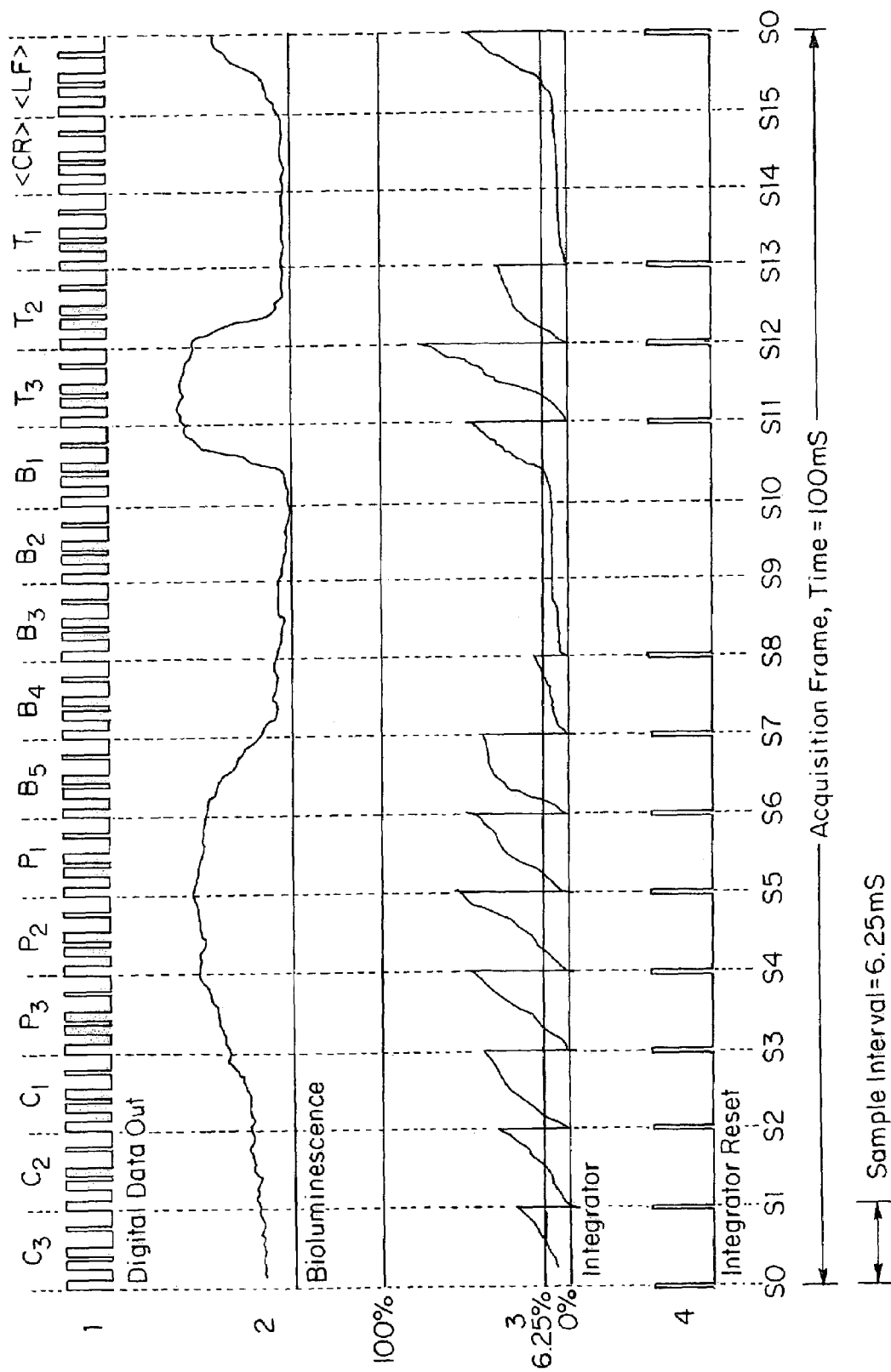
FIG. 6 is a plot of digital sampling protocol curves of the invention.

The sampling protocol used in accordance with the invention is shown in FIG. 6. The sampling timing is defined as the interval between individual data characters. Preferably the data will be in decimal ASCII form, as shown, but the software can be changed to output the data in a direct binary or hexadecimal form. Data output from the circuit are presented as unprocessed counts and are processed by a host computer (not shown) at the surface, although the programmability of the sensor would allow for calibration coefficients to be loaded into the sensor for real time processed output. In practical terms, however post processing at the surface in pseudo real time is quite satisfactory. An example data stream for a single light sensing detector is shown in curves FIG. 6 to be:

C3C2C1P3P2P1B5B4B3B2B1T3T2T1<CR><LF> where;

C3C2C1 is a repeating cyclical bit counter used to detect data dropouts (0 to 999), P3P2P1 is the pressure bytes (0 to 999), B5B4B3B2B1 is the bioluminescence bytes (0 to 65535), T3T2T1 is the temperature bytes (0 to 999), <CR><LF> is a delimiting carriage return bit and line feed bit.

FIG. 6 illustrates the timing for the sample interval and the integrator reset. Data is presented as a field or frame at 10 Hz. In the case shown, there are 16 ASCII characters or bytes making up the frame, thus the sampling interval (Sx) is 6.25 mS at 1200 Baud. If the integrator output is above the reset threshold, the values measured are summed into the B5B4B3B2B1 (bioluminescence) register in the microcontroller 112 and the integrator 142A (FIG. 5B) is reset. At timing intervals S9 and S10, the output of the integrator (see line 3) is below the reset threshold of 6–25% and consequently the integrator 142A is not reset, nor are these values summed into the total frame value. At S11 in the example, the value is added to the frame sum for bioluminescence. Temperature and pressure (not shown) are measured at every sampling interval regardless of integrator value. The measurements made during a frame are reflected in the next frames data string, thus the latency from measurement to output is 100 mS. By sampling the integrator at the individual bits that make up an ASCII character the dynamic range can be extended by a factor of 10. Increasing the baud rate can also increase the sampling frequency when using this protocol.

Photodiodes respond to a fairly wide range of wavelengths; the preferred sensor measures signals in the band of 400 to 800 nm. Optical filtering can be provided as appropriate for the specific bands of observations. The housing 22 is not limited to an envelope design. The circuit may be potted in a clear plastic material since no trimming of the circuit is required. The digital circuit of FIGS. 5A–B supports in circuit programming, so the only concern before potting is selecting the appropriate integrating capacitor setting.

The device may be attached to a vehicle which repeatedly moves vertically up and down from the sea surface to a depth of approximately 120 meters while being towed horizontally. Other sensors such as CTD's and fluorometers may also be mounted on such vehicles. From these observations, a vertical cross-section of the water body can be constructed, and the various attributes correlated. The sensor signals when processed and displayed produce a "patchy" distribution of bioluminescent organisms along a fourteen kilometer long profiles. The "patches" are commonly observed at fronts between water masses.

An expendable version of the bathyphotometer can be achieved by re-programming the microcontroller 112 to generate EIA 485 or FSK tones (Bell 202, for example) for transmission over a light gauge wire to a host interface on the surface for relaying to a GPS satellite receiver.

Figure 9:
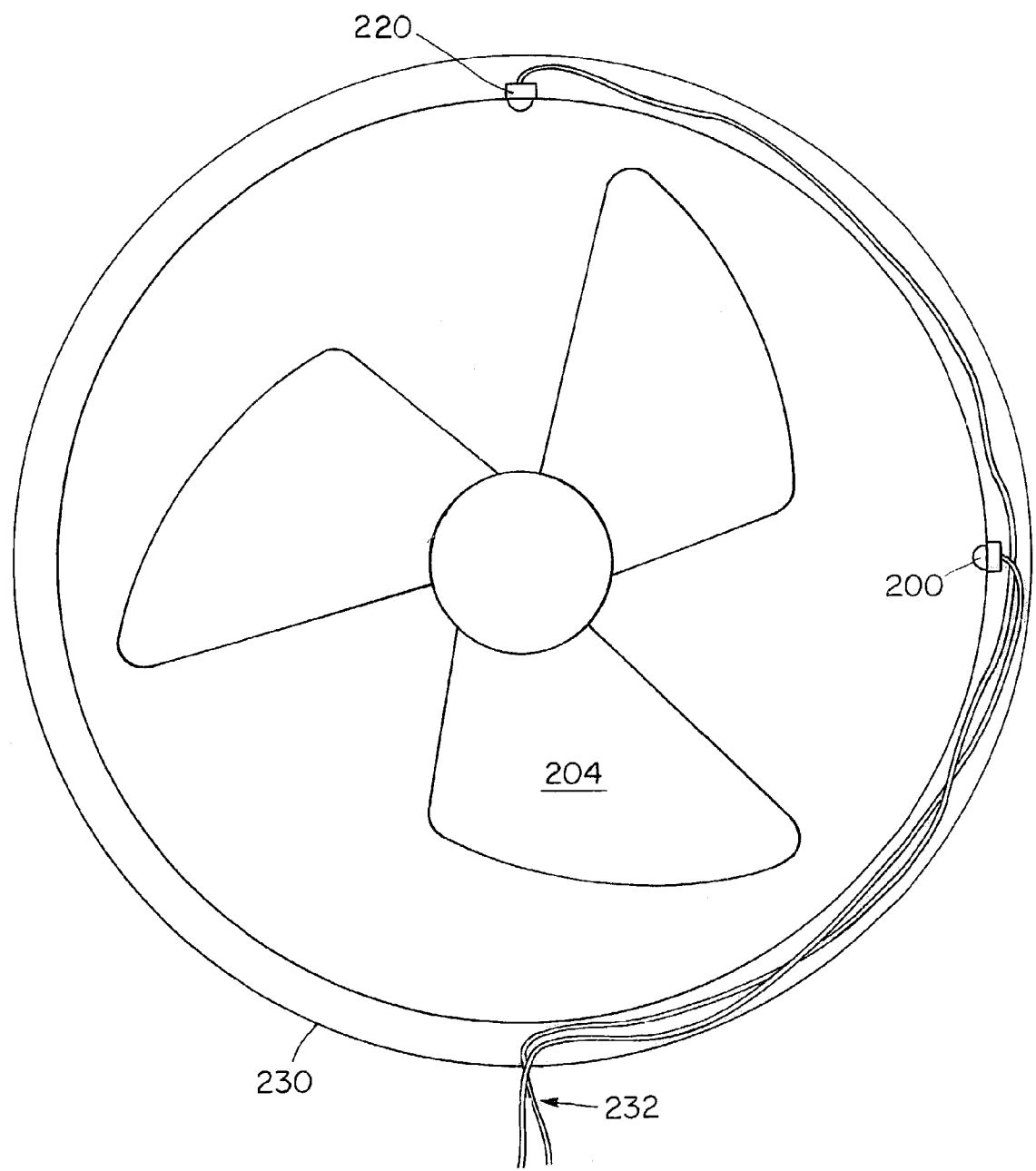
FIG. 9 is a front view of a shrouded propeller detector embodiment.

Another mode of deployment of the device 10 would be as a hard hull mounted on a surface ship, submarine, or an autonomous or remotely operated underwater vehicle. This version would offer lower drag, since it need not contain temperature and pressure sensors. These parameters are commonly available on the host vehicle, so the trade-off allows the sensor housing to be as small as possible to lower drag. Another alternative is to take advantage of the bioluminescence that is produced by the host vehicles propeller(s) and mount the sensor adjacent the propeller. In the case of an unshrouded propeller 204, as in FIG. 7, a digital detector 200 and 202, respectively, could be encapsulated in a clear plastic or glass housing that is embedded in the propeller mount 210 or hull 220 of the host vehicle 208. This system will provide a gross measurement of bioluminescence, useful for tracking fronts or detecting the threshold of detectable light as seen from the surface. The detectors 200 placed in the propeller mount are generally placed viewing aft. When a propeller is shrouded, the photodiodes 200 and 220 that make up a two zone sensor (with no practical limit on additional zones) could be embedded in the shroud 230 (FIG. 9) viewing the propeller 204. Coaxial leads 232 couple the photodiode signals to integrating amplifiers on board the host vehicle. For systems where the inside diameter of the shroud is less than 20 cm, a single detector may be adequate, for larger diameters, multiple detectors should be distributed throughout the housing to reduce the loss of measurable light due to $1/r^2$ extinction. The shrouded propeller offers the additional optical advantage that it confines the viewing area to a known volume.

Figure 10:
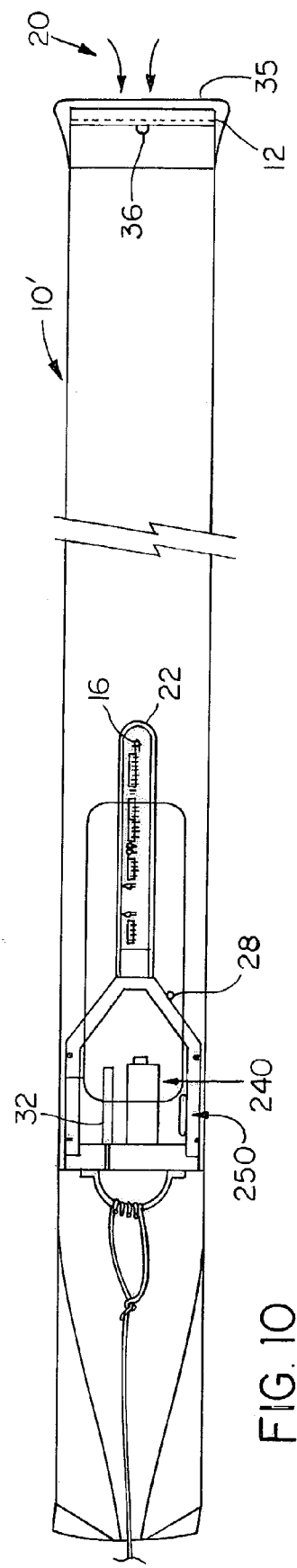
FIG. 10 is a side view of a self contained, internally logging, lowered embodiment.

Another mode of deployment would be on instrument packages lowered or free fall dropped vertically into the water column. Lowering and ascent rates are typically slower than horizontal traverses, sometimes requiring a different grid to achieve comparable excitation. A self contained device 10', that stores data internally is shown in FIG. 10, to include a 9 volt battery 240 which provides power for a number of profiles. Data may be transferred optically using the aforementioned optocouplers 102/104 of FIG. 5A through the glass pressure housing 22 eliminating the need for an electro-mechanical bulkhead connector or the need to open the case to off-load data. A magnetic reed switch 250 can be used to power up the instrument.

Figure 11:
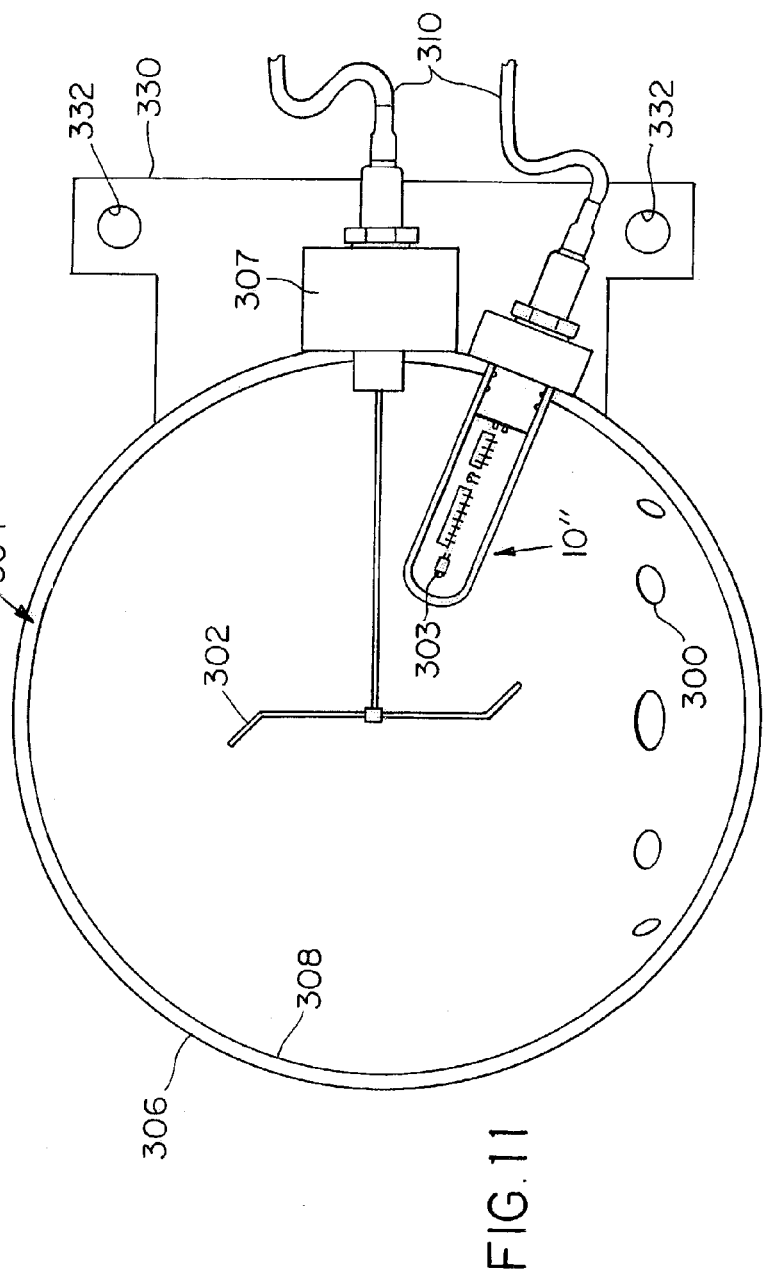
FIG. 11 is a schematic drawing of a moored embodiment.

By mechanically reconfiguring the sensor 10", it can be made to look into an integrating sphere 304 (FIG. 11) for low powered moored applications. A number of flutes or holes 300, about 2 cm in diameter are distributed around the lower half of the sphere to allow a natural exchange of water. A mechanical device 302, such as a propeller, periodically excited (say at 3.75 minute intervals) agitates the water mass, triggering bioluminescent activity. The excitation time is closely regulated (say 25 seconds), the total integrated light over that time is proportional to the amount of available bioluminescence.

Data from the sensors 303 are transmitted digitally over cable 310 to the host logging system. The analog version FIG. 2A of the sensor system would be suitable for this application, although it will require the data logging system at the surface host to digitize somewhere on the order of 10 Hz or greater. The outer surface 306 of the sphere 304 is made opaque by black paint and the inner surface 308 is white. Power for the motor 307 of the agitator 302 is supplied by the host via cable 310. Mounting bracket 330 is provided with bolt holes 332 for mooring the sphere 304.

The device of the invention is capable of providing the following features and advantages:
1. Low Cost of Fabrication: The fundamental circuit and housing materials cost are below $100. This enables the instrument to be manufactured at an affordable cost, that will allow wide spread use.
2. The analog embodiment of FIGS. 1–3 is easily interfaced to existing oceanographic data acquisition systems. Since it is an active detector, it overcomes the wire resistance Johnson noise and threshold limits of previous expendable designs.
3. The digital version of FIGS. 4–6 which includes: a microcontroller with communications and control routines provides an adaptable, re-programmable bioluminescence "engine" that also measures two other key parameters, temperature and pressure. By reconfiguring the mechanical design, a number of bioluminescence measuring problems can be solved. The "engine" can also be used to measure other optical or oceanographic properties. This engine solves the communications problem for long wire sensors.
4. The sampling routine used in the digital embodiment extends the low end sensitivity, as well as increasing the high end dynamic range.
5. Simplicity: The device uses readily available components that are easily second sourced. Manufacturing does not rely on high tech processes. The system can be easily assembled by hand.
6. Dual Zone Measurement: To overcome well understood optical emitter (bioluminescence) to detector limitations, a two zone measurement can be made. These synoptic measurements are also used to provide a fundamental kinetics measurement of bioluminescence. In certain applications, only one sensor is used, and the unused circuitry can be omitted.
7. Interchangable Chamber Geometries: The basic engine provides bioluminescence, temperature and pressure (depth) measurement data. Changing the chamber length or grid normally changes the drop rate in expendables. The direct pressure measurement negates the need to model drop rates for different geometries. The small housing size and large orifice reduces excitation before an organism passes through the sensor viewing chamber.
8. Low Power Consumption: The power requirements for the basic engine is less than 100 mW. The operating voltage can be as low as 2.7 V by selecting a different version microcontroller.
9. Compact Design: The overall length of the instrument 10 is approximately 50 cm, with an outside diameter of about 6 cm. Weight in the water is 300 grams. The basic sensor housing 22 can be as small as 10 cm, with a diameter of 3 cm. Surface mount technology will yield even a smaller sensor.
10. Expendable: The engine can be used to generate 1200 to 2400 Baud FSK tones for long wire (>1 km) applications or differential digital (similar to EIA-485) signals for digital data transmission. The low power requirements make coin battery type applications possible, and the economics of the design allow the device to be expendable.
11. Air Deployable: The expendable version is compact enough to be air deployed. Since this design uses FSK transmission, existing transmitters and receivers can be used.
12. Tow Vehicle Mounted: The basic compact design can be attached to a tow vehicle with little impact on drag and weight dynamics. The digital or analog output is interfaced to onboard data acquisition systems. For a dedicated tow system, the "engine" can send data digitally over two km of tow cable.
13. Autonomous Underwater Vehicle version: Two configurations for AUVs are possible. The first is a flow through design that has a low drag small chamber length. The second design takes advantage of the excitation of bioluminescent organisms by the propeller of the AUV (when appropriate).
14. Moored Version: In this version the engine is directed into a sphere with a white interior. This geometry is known in optical terms as an "integrating sphere". A motor turns an agitator to stimulate bioluminescent activity. This is performed at regular intervals. Small holes on the bottom of the sphere allow a natural exchange of water.
15. Hull Mounted Version: This version can be mounted either through the hull, in line with the sea chest for example, or in an exterior compact design to allow real time underway surface measurements.
16. Graphical Display Software: A real time display program has been developed. It displays drop rate, forward viewing bioluminescence, aft viewing bioluminescence, temperature, location, and other record keeping statistics.
17. Hand Held: A compact detector can be contained in an enclosure with a motor driven agitator. Data is displayed with light emitting diodes and is logged internally.
18. Self Contained Data Logging Version: A self powered photometer records data internally for later downloading. An optical link eliminates the need to open up the case or have any external electro-mechanical connectors.
19. Lends Itself to Other Expendable Probes: The digital communications platform developed can be also used to measure optical light extinction, turbidity, light or sound adsorption, light or sound attenuation, sound velocity, conductivity, high resolution temperature, turbulence (hot wire anemometery), ambient noise, etc. Since the probe supports local optical communication, a "smart" launcher is an improvement over existing art.

20. FSK Generating Software Routines: As part of the engine software, programs have been written to generate FSK tones in software eliminating the need for a hardware modem in the probe.
21. Simplicity in fabrication, deployment and maintenance.
22. Ability to deploy and recover safely in heavy seas due to its small size, light weight, and great strength.
23. Robustness of Sensor and Electronics: Not readily damaged by the high mechanical vibrations encountered in many deployments.
24. Ability to calibrate and hold calibration.
25. Broadband sensitivity: Easy to adapt for broad or narrow band use.
26. Flexibility of Data Stream Handling and Processing: Can be programmed appropriate to the application.
27. Ease of Integration With Other Type of Sensors: "Plug and Play" with commercially-available digital data recording systems.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. An expendable oceanographic digital communications system, comprising:
   a housing;
   at least one sensor disposed in the housing for sensing oceanographic properties of a body of water while the housing descends in the body of water; an active depth measuring device disposed in the housing for providing depth data associated with the descent of the housing;
   a reprogrammable microcontroller disposed in the housing and coupled to the sensor and the active depth measuring device, the reprogrammable microcontroller integrates digital data from the sensor and the active depth measuring device into an integrated digital data stream based on a sampling protocol, the sampling protocol including a cyclical bit counter for detecting data dropouts; and
   a cable spool disposed in the housing having one end coupled to the reprogrammable microcontroller for communicating the combined digital data stream to a host computer.

2. The system of claim 1, wherein the active depth measuring device is a pressure sensor.

3. The system of claim 1, further comprising an output line driver coupled between the reprogrammable microcontroller and the cable, wherein the output line driver is a balanced output line driver.

4. The system of claim 1, wherein the cable is a bifilar wire.

5. The system of claim 1, wherein the cable is a single conductor wire.

6. The system of claim 1, wherein the sensor is an optical light extinction sensor, a turbidity sensor, a light sensor, a light attenuation sensor, a sound attenuation sensor, a sound velocity sensor, a conductivity sensor, a high resolution temperature sensor, a turbulence sensor, a bioluminescence sensor, or an ambient noise sensor.

7. The system of claim 1, further comprising at least another sensor for sensing a different common oceanographic property than the sensor.

8. The system of claim 1, wherein the digital data is continuously transmitted to the host computer as the sensor descends in a body of water.

9. The system of claim 1, wherein the reprogrammable microcontroller generates tones representing the combined digital data stream for transmission over the cable.

10. The system of claim 9, wherein the tones generated are EIA 485 tones or FSK tones.

11. The system of claim 1, further comprising a power supply is positioned within the housing, the at least one sensor, the active depth measuring device, and the reprogrammable microcontroller being powered entirely by the power supply, the power supply supplying a voltage of less than about 10 V and having a maximum power output of less than about 100 mW.

* * * * *